United States Patent [19]

Chabert et al.

[11] 3,989,843

[45] Nov. 2, 1976

[54] EMULSIFICATION OF FLUOROCARBON COMPOUNDS FOR BIOLOGICAL APPLICATION AS OXYGEN TRANSPORTERS

[75] Inventors: Pierre Chabert, Saint Genis Laval; Louis Foulletier; André Lantz, both of Oullins, all of France

[73] Assignee: Produits Chimiques Ugine Kuhlmann, Paris, France

[22] Filed: Oct. 22, 1974

[21] Appl. No.: 516,899

[30] Foreign Application Priority Data
Nov. 7, 1973  France .............................. 73.39533

[52] U.S. Cl. .............................. 424/325; 424/285; 424/342; 424/350; 424/351; 424/352; 424/353
[51] Int. Cl.² .......................................... A61K 31/13
[58] Field of Search ........... 424/351, 352, 342, 325, 424/285, 350

[56] References Cited
OTHER PUBLICATIONS
Chemical Abstracts 73:86283m (1970).
Chemical Abstracts 71:122152n (1969).

*Primary Examiner*—Leonard Schenkman
*Attorney, Agent, or Firm*—Pennie & Edmonds

[57] ABSTRACT

Aqueous emulsions of polyfluorinated organic compounds useful as physiological transporters of oxygen, particularly in saline solutions isotonic with blood, are prepared by a method which comprises mixing a polyfluorinated compound with water or aqueous saline solution in the presence of at least one predominantly lipophilic polyfluorinated emulsifier and also at least one predominantly hydrophilic polyfluorinated emulsifier.

7 Claims, No Drawings

3,989,843

EMULSIFICATION OF FLUOROCARBON COMPOUNDS FOR BIOLOGICAL APPLICATION AS OXYGEN TRANSPORTERS

BACKGROUND OF THE INVENTION

This invention provides a new method for preparing emulsions of fluorocarbon compounds in water and its saline solutions. These emulsions have numerous applications particularly in pharmacy. Their ability to transport oxygen makes them especially useful as a substitute for red blood corpuscles.

The possibility of using fluorinated organic compounds as a blood substitute has been under study since L. C. Clark and F. Gollan (Science 152, 1755(1966)) first succeeded in maintaining mice alive while being immersed in a fluorocarbon liquid saturated with oxygen. Because of the then demonstrated large solubility of oxygen and carbon dioxide in fluorocarbons, there has rapidly followed a succession of attempts to replace blood wholly or in part by such liquids with the purpose of making them perform the functions of transporting oxygen and eliminating carbon dioxide.

Since fluorocarbons are not miscible with blood, it is not possible to inject them as such. H. A. Sloviter and T. Kamimoto (Nature, 216, 458 (1967)) and R. P. Geyer (Federation Proceedings, 27, 952 (1968)) conceived the idea of emulsifying the fluorocarbon in water or in saline water and were thus able to obtain fluids compatible with blood. In this way the complete or partial exchange of the blood of mice or dogs could be achieved with success.

However there is still a problem to convert the fluorocarbon into an emulsion with particles sufficiently fine to avoid risk of clogging the finest capillaries. The emulsion must furthermore be stable over long periods of time and must be compatible with blood plasma or with fluids of similar structure. The dispersions are in general achieved with the aid of a surface active agent and the best results thus far have been obtained with nonionic surfactants of polymeric type derived from polyoxyethylene and polyoxypropylene, known commercially under the name PLURONIC. In particular the PLURONIC F68, stated by its commercial supplier to contain 80% ethylene oxide and 20% propylene oxide has been utilized by R. P. Geyer. A standard preparation is made by dispersing 15 to 30% of a fluorocarbon compound and 2.5 to 10% of the surfactant in a physiological saline solution having an ionic composition identical with that of blood.

The formation of such emulsions, however, requires a huge quantity of energy which is generally provided by an ultrasonic generator. The emulsion can also be obtained with a pressurized homogenizer, exemplarily of the Manton Gaulin type (See the Green Cross Corp., Offenlegungsschrift 2,114,094 dated Sept. 2, 1971). These two types of preparation make possible the obtainment of very fine-particled emulsions from which any larger particles present must be separated, as by ultracentrifugation. But these techniques are extremely difficult to carry out and have the additional disadvantage of requiring such high magnitudes of energy that some carbon-fluorine bonds are broken during the process with the resultant formation of small but significant quantities of toxic fluoride ions.

Also, when the emulsions obtained by these mechanical or ultrasonic methods are sufficiently fine, with particle size cleanly limited to less than one micron, they are invariably characterized by troublesome high viscosity. (Science, 179, 669 (1973)).

The presence of fluoride ions, whose level can reach 200 ppm in emulsions prepared by ultrasonic techniques, necessitates cumbersome subsequent purification steps. Thus the toxicity of such emulsions has been diminished by treatments with ion-exchange resins. (See L. Clark, Triangle Vol. XIII No. 2, 85–96 (1973)). The future use of fluorocarbon emulsions as blood substitutes holds promise only if a more practical method of emulsification is available which does not involve the above described disadvantages.

SUMMARY OF THE INVENTION

A means has now been found whereby fluorocarbon compounds can be emulsified in water or saline solutions without the necessity of mechanical or ultrasonic homogenization and without the above-described disadvantages of prior procedures.

Briefly stated, the method of the present invention comprises mixing a polyfluorinated organic compound with water or aqueous saline solution in the presence of at least one predominantly lipophilic polyfluorinated emulsifier and also at least one predominantly hydrophilic polyfluorinated emulsifer.

The preferred emulsifers are nonionic surfactants having the formula $C_mF_{2m+1}-(CH_2)_a-O-(CH_2CH_2O)_n-H$ wherein $m$ is 4 to 10, $C_mF_{2m+1}$ is linear or branched, $a$ is 1 to 4, $n$ is 1 to 5 for predominantly lipophilic emulsifiers and $n$ is 6 to 40 for predominantly hydrophilic emulsifers.

The preferred embodiment of the method of this invention comprises mixing said polyfluorinated organic compound, said emulsifiers and said water or aqueous saline solution; heating the mixture, with stirring, to about 70° C or higher; and cooling the heated mixture with continued stirring until a transparent emulsion is formed.

DETAILED DESCRIPTION

It is well-known that emulsions are disperse systems of two immiscible liquids, one being dispersed in the other in the form of fine particles or droplets owing to the presence of an emulsifier. An emulsifier molecule characteristically has two parts one of which is more soluble in the dispersed phase, the other of which is more soluble in the dispersing phase. In the case of an oil-and-water emulsion the part more soluble in the dispersed oil phase is known as the lipophilic part and the part more soluble in water is known as the hydrophilic part. The emulsifier molecules are oriented on the interface of the dispersed droplets. Thus with an oil-in-water emulsion the hydrophilic part is turned outward to the water and the hydrophobic or lipophilic part is turned inward to the oil droplet. While it is appreciated that ease of emulsification generally depends on the relative proportion of the two parts, many unpredictable factors also are involved, as evidenced by the above-described deficiencies of the prior-art emulsions of fluorocarbons in water.

In searching for a better emulsifer for fluorocarbons, it first occurred to the present inventors to use emulsifiers whose lipophilic part is fluorinated so as to enhance its solubility in the fluorocarbon to be emulsified. Indeed, they were successful in obtaining excellent emulsions with nonionic surfactants having the formula $C_mF_{2m+1}(C_2H_4O)_nH$ wherein $m$ was 6 and 8 and $n$ was 10 to 20. However, just as in the case of nonfluorinated emulsifiers of the prior art, these emulsifiers having perfluorinated alkyl radicals would not give stable emulsions unless they were submitted to either mechanical homogenization or ultrasonic treatment.

However, present inventors have now established, completely unexpectedly, that is it is possible to prepare very stable aqueous emulsions of fluorocarbons very easily by using, instead of one fluorinated emulsifier, at least two fluorinated emulsifiers one of which has a predominantly hydrophilic character (i.e. a relatively high hydrophile-lipophile balance, HLB) and the other of which has a predominantly lipophilic character (relatively low HLB). In this manner it is possible to prepare an emulsion without recourse to either violent agitation or ultrasonics.

In preparing an emulsion according to the present invention, a quantity of fluorinated surfactant mixture containing a low-HLB fraction and a high-HLB fraction is introduced into a vessel containing the fluorocarbon to be emulsified and the dispersing phase, i.e. water or aqueous saline solution. The mixture is then heated to a temperature higher than about 70° C, and allowed to cool with agitation. There is thus obtained an emulsion which becomes transparent on reaching a certain threshold temperature and which remains transparent as the emulsion is allowed to cool further until a second threshold temperature is reached at which the emulsion loses its transparency. The range of temperature between the two thresholds, which can be called the transparency domain, can be modified by changing the relative amounts of the respective surfactants used.

The formation of the transparent emulsion on cooling can be effected regardless of the type or speed of agitation used. In the preparation of small quantities of emulsions, for example 100 to 1000 ml., a laboratory-type magnetic stirrer is quite satisfactory.

When the transparent emulsion is kept at a temperature between the two threshold temperatures, it can be filtered easily through a Millipore filter having 0.22 micron apertures at a pressure differential of about 0.5 atmosphere.

The emulsions of this invention can be sterilized by heating to 110°–115° C for a period of 15 minutes. This heating causes separation of the phases but the emulsion forms again very easily by simple recooling to a temperature within the transparency domain, i.e. within the stability range between said threshold temperatures.

When kept at a temperature within the transparency domain, the emulsions of this invention are very stable. Their particle size has been determined by electron microscopy, using the carbon replica technique. Substantially all the particles have size less than 0.1 micron and the emulsions remain stable for at least several weeks without increase in particle size.

On cooling below the stability range of temperature an emulsion gradually becomes milky, then undergoes sedimentation. These changes, however, are completely reversible and the transparent emulsion can be formed again simply by heating, with stirring, to a temperature within the stability range of temperature. As already mentioned in discussing sterilization, the transparent emulsion is disturbed by heating, and becomes separated into phases, but this transformation is reversible.

The emulsions can be stored over a period of several months either at a temperature at which they remain stable or at a lower temperature at which they undergo sedimentation. In the latter case, even after storage prolonged over several months, it is possible to obtain fresh transparent emulsion by simple heating with gentle agitation.

In order to prepare emulsions usable as blood substitutes the concentration of fluorinated substance must be sufficient to obtain a good amount of dissolved oxygen and of carbon dioxide without undue increase in the viscosity of the mixture. The best results in this respect have been obtained with emulsions containing about 10 to 30% by volume of polyfluorinated carbon compounds. The instant emulsification procedure achieves obtaining such emulsions as well as emulsions containing more or less of the dispersed phase, as for example from about 5 to 35% by volume. To accomplish this it is suitable to use about 5 to 20% of surfactant mixture based on the weight of water or aqueous saline solution. In general, the weight ratio of predominantly hydrophilic surfactant to predominantly lipophilic surfactant used in carrying out this invention is from about 1/1 to 2.5/1, the most suitable range being from about 1.5/1 to 2.0/1.

The polyfluorinated carbon compounds useful according to this invention are organic compounds entirely or almost entirely fluorinated, those which are substantially perfluorinated being the most suitable; they are chemically inert, immiscible in water, non-toxic and with vapor pressure sufficiently low as to avoid evaporation within the circulatory system.

A particular requirement is that the emulsified polyfluorinated compound should dissolve a quantity of oxygen commensurate with that dissolved by blood. The polyfluorinated compound should also be a solvent for carbon dioxide, but this presents no problem because any compound which dissolves sufficient oxygen also dissolves sufficient carbon dioxide, which is extremely soluble in all fluorocarbons.

Emulsifiable fluorinated compounds which serve as the dispersed phase of the emulsions of this invention include perfluorobutylamine, perfluorinated butyltetrahydrofuran, perfluorooctane, perfluoronaphthalene, perfluoromethylnaphthalane; 1,1,2-trihydro-perfluoro-1-decene; 1,1,1,2,2 pentahydro-perfluorodecane and, in particular, substances having the formula $$C_pF_{2p+1}-CH=CH-C_qF_{2q+1}$$

wherein $p$ and $q$ are identical or different whole numbers from 2 to 10 and wherein their sum $(p+q)$ is equal to or greater than 8.

Among this last category, there are specially preferred 1,2-di(perfluorohexyl)ethylene and 1-perfluorobutyl-2-perfluorooctyl ethylene having the respective formulas $C_6F_{13}CH=CH$ 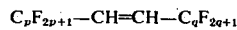 $C_6F_{13}$ and $C_4F_9CH=CH$ $C_8F_{17}$.

The higher homologs of these substances are solid products such as when $n = m = 8$, the melting point is 56° C. On emulsification, these solid substances yield creams which are useful in pharamacy and cosmetology.

The solubility of oxygen in the recited polyfluorinated compounds is of the order of 40 to 60 volumes of gas per 100 volumes of compound at 37° C and one atmosphere. Exemplarily perfluorotributylamine dissolves 45%, by volume, of oxygen; and 1,2-di(perfluorohexyl)ethylene dissolves 48.5%. The solubilities of carbon dioxide in these two substances are 162% and 230% respectively.

In order to be useful in contact with blood, the surfactants used in carrying out the method of this invention must be nonionic. Stable emulsions made with corresponding polyfluorinated anionic and cationic surfactants have been found to be unsatisfactory, almost all of them being incompatible with blood, causing hemolysis.

Suitable nonionic surfactants are those having the formula $$C_mF_{2m+1}-(CH_2)_a-O-(CH_2CH_2O)_nH \qquad (A)$$

wherein $C_mF_{2m+1}$ is a straight or branched chain, $m$ is 4 to 10, $a$ is 1 to 4, $n$ is 1 to 5 for predominantly lipophilic emulsifiers and $n$ is 6 to 40 for predominantly hydrophilic emulsifiers. These materials are easily prepared from the corresponding alcohols $C_mF_{2m+1}(CH_2)_a$ OH by well-known methods of ethoxylation using ethylene oxide.

According to the emulsification method of this invention, at least one predominantly lipophilic and at least one predominantly hydrophilic surfactant are used in admixture with the polyfluorinated compound to be emulsified and the aqueous dispersing phase. The respective components of the mixture can be added to each other in any sequence, before heating.

The surfactant composition can also be described, particularly pertinently when more than one surfactant of either or both HLB types are used, as being composed of two fractions, a predominantly lipophilic fraction and a predominantly hydrophilic fraction.

The surfactant mixtures can be formulated from well defined chemical substances obtained by physical separation from a mixture of ethoxylated substances corresponding to formula (A) above but having a variety of values of $n$. When $n$ is low, exemplarily 1 to 5, such products can easily be obtained by fractional distillation.

The surfactants can also be mixtures of products corresponding to a range in extent of condensation with ethylene oxide. The distribution of $n$ can, for example, correspond approximately to Poisson's Law. When such a mixture is used representing a range in molecular weight, the overall composition can conveniently be designated by a formula such as (A) wherein $n$ now signifies an average or mean value. Such mixtures can be used for both low-HLB and high-HLB fractions of the surfactant composition.

Thus, for example, a mixture of surfactants can be derived by ethoxylation of 2-perfluorohexyl-ethyl alcohol $C_6F_{13}C_2H_4OH$ having the number of condensed ethoxy groups varying over the range 0 to 5 with an average value of $n$ in equation (A) equal to 2.8. Such a mixture can be represented by the formula $C_6F_{13}C_2H_4O(C_2H_4)_{2.8}$ H, or alternatively by $C_6F_{13}(C_2H_4 O)_{3.8}H$. Such a mixture is shown in the Examples 5, 7 and 8 below to function satisfactorily as the low-HLB component of an emulsifier system of this invention.

In the case of the high-HLB fraction, it is particularly advantageous to be able to use mixtures as such procedure avoids the purification steps which become more tedious as $n$ increases.

Types of surfactants which have given particularly excellent results are $$C_6F_{13}C_2H_4 \ O(CH_2CH_2O)_nH$$

and $$C_6F_{13}C_3H_6 \ O(CH_2CH_2O)_nH$$

wherein $n$ is 1 to 5 for the low-HLB fraction and $n$ is 6–40, most suitably 10 to 20 for the high-HLB fraction.

Other types of useful surfactants can be prepared by condensing polyfluorinated alcohols with propylene oxide or with mixtures of propylene oxide and ethylene oxide. The products of propoxylation are particularly interesting as examples of the low-HLB type of surfactant.

The total amount of emulsifiers which is most suitable depends on the type of emulsion desired, the respective proportions of dispersed and dispersing phases, the fluorinated substance to be dispersed and the nature of the dispersing phase, i.e. whether plain water or saline. In general, emulsions containing about 20–30% by volume of dispersed phase are most suitably prepared with about 5 to 15% total emulsifier based on the weight of the aqueous phase, while emulsions containing about 15–25% of dispersed phase are generally suitably prepared with about 5–10% total emulsifier. However, each set of parameters can be optimized by preliminary experimentation.

The relative proportions of predominantly lipophilic and predominantly hydrophilic surfactants can likewise be varied over a wide range with resulting benefits of this invention. Again, the optimum range of this ratio for any particular combination of parameters can be determined by preliminary experimentation. Among the factors influencing this optimum are the nature of the surfactants themselves, the nature of the compound to be emulsified and again the composition of the dispersing phase. In general, however, satisfactory results are obtained when the ratio of mainly hydrophilic to mainly lipophilic fractions is maintained within the ranges recited earlier herein. Among other aspects, the respective proportions of the surfactants used influences the transparency domain, i.e. the zone of temperature in which the emulsion remains stable.

The use of substantial quantities of highly fluorinated emulsifiers as is characteristic of the method of this invention also enhances the solubility of oxygen in the emulsion. The solubility of oxygen in the described nonionic polyfluorinated surfactants is of the order of 20 to 35% by volume. Thus, exemplarily, $C_6F_{13}(C_2H_4O)_3H$ dissolves 29 volume percent of oxygen at 37° C and $C_6F_{13}(C_2H_4O)_{12}H$ dissolves 25 volume percent of oxygen at the same temperature. The corresponding solubilities of carbon dioxide in these two surfactants are respectively 175 and 217 volume percent.

This invention will be further illustrated by description in connection with the following specific examples of the practice of it wherein, as also elsewhere herein, proportions are in parts by weight unless stated otherwise.

EXAMPLE 1

Into a glass reactor there is added 800 ml. of a physiological saline solution having the following composition, which is isotonic with blood and commonly used in pharmacology for purposes of cardiac survival:

| COMPONENT | GRAMS PER LITER OF TOTAL AQUEOUS SOLUTION |
|---|---|
| NaCl | 8. |
| KCl | 0.2 |
| $CaCl_2.2H_2O$ | 0.265 |
| $MgCl_2.6H_2O$ | 0.100 |

| COMPONENT | GRAMS PER LITER OF TOTAL AQUEOUS SOLUTION |
|---|---|
| $NaH_2PO_4.H_2O$ | 0.050 |
| $NaHCO_3$ | 1. |

There is then added also 200 ml. of 1,2-diperfluorohexyl ethylene $C_6F_{13}-CH=CH-C_6F_{13}$ and 67.5 grams of an emulsifying mixture containing 38.5% of a distilled pure compound having the formula $C_6F_{13}(C_2H_4O)_3H$ and 61.5% of a mixture of polyethoxylated 2-perfluorohexyl-ethyl alcohols having the average formula $C_6F_{13}(C_2H_4O)_{12.3}H$.

The mixture is first heated to 70° C and then allowed to cool slowly with gentle agitation with the aid of a magnetic stirrer. A transparent emulsion is obtained in the temperature interval of 40°–35° C. While the temperature is maintained in the range of 35°–40° C the emulsion is filtered through a millipore filter of 0.22 micron aperture size. This filtration is carried out easily without leaving any residue on the filter, taking about 1 hour to pass through a filter 40 mm in diameter at a pressure gradient of about 0.4 atmospheres.

On the other hand, this emulsion does not pass through a filter having pore size 0.1 micron.

The determination of particle size by electron microscopy confirms the observations in the filtration tests, particles having dimensions greater than 0.2 microns being substantially absent.

This emulsion has a maximum vicosity of 5.12 centipoises at 38° C. The solubility of oxygen at 37° C, based on weight of emulsion, is 15% and the corresponding solubility of carbon dioxide is 90%. At this temperature, the specific mass of the emulsion is 1.51 grams/ml.

EXAMPLE 2

The method of example 1 is followed using the same quantities of saline solution and diperfluorohexyl ethylene, but using 68.5 grams of the same emulsifiers in the ratio 38% of the $C_6F_{13}(C_2H_4O)_3H$ and 62% of the $C_6F_{13}(C_2H_4O)_{12.3}H$. A transparent emulsion is obtained in the temperature interval 45°–38° C.

EXAMPLE 3

Using the same procedure as in example 1, an emulsion is prepared from
  80 ml distilled water
  20 ml $C_6F_{13}-CH=CH-C_6F_{13}$
  2.4 grams $C_6F_{13}(C_2H_4O)_3H$
  4.45 $C_6F_{13}(C_2H_4O)_{20}H$.
A transparent emulsion is obtained in the temperature interval 35°–40° C.

EXAMPLE 4

4a. Using the same procedure as in example 1, an emulsion is prepared from
  80 ml distilled water
  20 ml $C_6F_{13}CH=CH-C_6F_{13}$
  2.4 grams $C_6F_{13}(C_2H_4O)_3H$
  4.4 grams $C_6F_{13}(C_2H_4O)_{12.3}H$.
A stable and transparent emulsion is obtained between 35° and 42° C.

4b. The emulsion obtained in 4a is mixed additionally with 2.3 grams $C_6F_{13}(C_2H_4O)_3H$ and 4.5 grams $C_6F_{13}(C_2H_4O)_{12.3}H$ and again heated to about 70° C. On recooling with continued stirring it is found that the temperature zone of transparency has now changed to 60°–52° C.

EXAMPLE 5

Using the same procedure as in example 1, an emulsion is prepared from
  80 ml distilled water
  20 ml of $C_6F_{13}CH=CH-C_6F_{13}$
  3.8 grams of a high-hydrophilic surfactant mixture having the average composition $$C_6F_{13}(C_2H_4O)_{12.3}H$$

and 3.4 grams of a low hydrophilic surfactant mixture having the weight-average composition $$C_6F_{13}(C_2H_4O)_{3.8}H$$

being composed of six surfactants $$C_6F_{13}(C_2H_4O)_sH \text{ or } C_6F_{13}C_2H_4O(C_2H_4O)_nH$$

distributed in the following manner:

| s | n | % |
|---|---|---|
| 1 | 0 | 7 |
| 2 | 1 | 6 |
| 3 | 2 | 7 |
| 4 | 3 | 65 |
| 5 | 4 | 13 |
| 6 | 5 | 2 |

The emulsion obtained has a transparency domain from 35° to 42° C.

EXAMPLE 6

Using the same procedure as in example 1, an emulsion is prepared from:
  80 ml distilled water
  20 ml perfluorooctane $C_8F_{18}$
  2.3 grams $C_6F_{13}(C_2H_4O)_3H$
  4.1 grams $C_6F_{13}(C_2H_4O)_{12.3}H$ mixture
The interval of temperatures at which the resulting emulsion is stable and transparent is 20° to 25° C.

EXAMPLE 7

Using the same procedure as in example 1, an emulsion is prepared from
  80 ml distilled water
  20 ml 1,1,2 trihydro-perfluoro-1-dexene (or perfluoro-n-octylethylene, $C_8F_{17}-CH=CH_2$)
  4 grams $C_6F_{13}(C_2H_4O)_{12.3}H$ mixture
  2.8 grams $C_6F_{13}(C_2H_4O)_{3.8}H$ mixture as described in example 5.
The emulsion thus obtained is transparent between 20° and 40° C.

EXAMPLE 8

Using the same procedure as in example 1, an emulsion is prepared from
  80 ml distilled water
  20 ml perfluorotributylamine
  4.1 grams $C_6F_{13}(C_2H_4O)_{12.3}$ H mixture
  2.7 grams $C_6F_{13}(C_2H_4O)_{3.8}H$ mixture as described in example 5.
The obtained emulsion is transparent and stable in the temperature range 30° to 42° C.

When the same preparation is made except that the amounts of the emulsifiers used are 4.0 grams $C_6F_{13}(C_2H_4O)_{12.3}H$ mixture
2.4 grams $C_6F_{13}(C_2H_4O)_{3.8}H$ mixture as described in example 5, the obtained emulsion has a stability zone between 45° C and 50° C.

EXAMPLE 9

Using the same procedure as in example 1, an emulsion is prepared from 80 ml distilled water
20 ml $C_8F_{17}-CH=CH-C_4F_9$
2.4 grams $C_6F_{13}(C_2H_4O)_3H$
4.3 grams $C_6F_{13}(C_2H_4O)_{12.3}H$ mixture.

The obtained emulsion is transparent and stable between 34° and 43° C.

We claim:

1. A method of preparing an aqueous oxygen-transporting emulsion suitable for injection into the bloodstream which comprises
   i. combining water with from about 5 to 35% by volume base on the water of a polyfluorinated carbon compound which is perfluorobutylamine, perfluorotributylamine, perfluorinated butyltetrahydrofuran, perfluorooctane, perfluoronaphthalene, perfluoromethylnaphthalene, 1,1,2-trihydroperfluoro-1-decane, 1,1,1,2,2-pentahydroperfluorodecane or a substance having the formula $$C_pF_{2p+1}-CH=CH-C_qF_{2q+1}$$

wherein $p$ and $q$ are identical or different whole numbers from 2 to 10 and wherein their sum ($p+q$) is equal to or greater than 8; and a mixture of polyfluorinated surfactants whose total weight is from about 5 to 20% of the weight of the water, said mixture containing (1) predominantly hydrophilic surfactants (H) of the formula:

$$C_mF_{2m+1}-(CH_2)_a-O(CH_2CH_2O)_nH$$

wherein $m$ is 4 to 10, $C_mF_{2m+1}-$ is linear or branched, $a$ is 1 to 4, and $n$ is 6 to 40, and (2) predominantly lipophilic surfactants (L) of the formula:

$$C_mF_{2m+1}-(CH_2)_a-O(CH_2CH_2O)_nH$$

wherein $m$ is 4 to 10, $C_mF_{2m+1}-$ is linear or branched, $a$ is 1 to 4, and $n$ is 1 to 5; the weight ratio of hydrophilic surfactants to lipophilic surfactants is from about 1/1 to 2.5/1, ii. heating said emulsifiable composition, with stirring, to at least about 70° C and
   iii. cooling the heated composition with continued stirring until a transparent emulsion is formed.

2. The method of claim 1 wherein each of the emulsifiers has the formula $$C_6F_{13}-C_2H_4-O(C_2H_4O)_nH.$$

3. The method of claim 1 wherein the emulsified polyfluorinated compound is $C_6F_{13}-CH=CH-C_6F_{13}$.

4. The method of claim 1 wherein the emulsified polyfluorinated compound is perfluorotributylamine.

5. The method of claim 1 wherein the emulsifiable composition also contains salts which render the emulsion isotonic with blood.

6. An aqueous oxygen-transportation emulsion suitable for injection into the bloodstream which comprises water, a polyfluorinated carbon compound in an amount of from about 5 to 35% by volume of the water which is perfluorobutylamine, perfluorotributylamine, perfluorinated butyltetrahydrofuran, perfluorooctane, perfluoronaphthalane, perfluoromethylnaphthalane, 1,1,2-trihydro-perfluoro-1-decane, 1,1,1,2,2-pentahydroperfluorodecane, or a substance having the formula $$C_pF_{2p+1}-CH=CH-C_qF_{2q+1}$$

wherein $p$ and $q$ are identical or different whole numbers from 2 to 10 and wherein their sum ($p+q$) is equal to or greater than 8, and a mixture of nonionic polyfluorinated surfactants whose total weight is from about 5 to 20% of the weight of the water, said mixture containing (1) predominantly hydrophilic surfactants (H) of the formula:

$$C_mF_{2m+1}-(CH_2)_a-O(CH_2CH_2O)_nH$$

wherein $m$ is 4 to 10, $C_mF_{2m+1}-$ is linear or branched, $a$ is 1 to 4, and $n$ is 6 to 40 and (2) predominantly lipophilic surfactants (L) of the formula:

$$C_mF_{2m+1}-(CH_2)_a-O(CH_2CH_2O)_nH$$

wherein $m$ is 4 to 10, $C_mF_{2m+1}-$ is linear or branched, $a$ is 1 to 4 and $n$ is 1 to 5; the weight ratio of the hydrophilic surfactants to lipophilic surfactants is from about 1/1 to 2.5/1.

7. The method of promoting the transport of oxygen in the bloodstream which comprises injecting into said bloodstream an effective amount of an aqueous emulsion which contains water, from about 5 to 35% by volume of the water of a polyfluorinated carbon compound which is perfluorobutylamine, perfluorotributylamine, perfluorinated butyltetrahydrofuran, perfluorooctane, perfluronaphthalane, perfluoromethylnaphthalane, 1,1,2-trihydro-perfluoro-1-decane, 1,1,1,2,2-pentahydroperfluorodecane, or a substance having the formula:

$$C_pF_{2p+1}-CH=CH-C_qF_{2q+1}$$

wherein $p$ and $q$ are identical or different whole numbers from 2 to 10 and wherein their sum ($p+q$) is equal to or greater than 8, and a mixture of nonionic polyfluorinated surfactants whose total weight is from about 5 to 20% of the weight of the water, said mixture containing (1) predominantly hydrophilic surfactants (H) of the formula:

$$C_mF_{2m+1}-(CH_2)_a-O(CH_2CH_2O)_nH$$

wherein $m$ is 4 to 10, $C_mF_{2m+1}-$ is linear or branched, $a$ is 1 to 4, and $n$ is 6 to 40, and (2) predominantly lipophilic surfactants (L) of the formula:

$$C_mF_{2m+1}-(CH_2)_a-O(CH_2CH_2O)_nH$$

wherein $m$ is 4 to 10, $C_mF_{2m+1}-$ is linear or branched, $a$ is 1 to 4 and $n$ is 1 to 5; the weight ratio of hydrophilic surfactants to lipophilic surfactants is from about 1/1 to 2.5/1.

* * * * *

UNITED STATES PATENT OFFICE
CERTIFICATE OF CORRECTION

Patent No. 3,989,843 - Dated November 2, 1976

Inventor(s) Pierre Chabert et al.

It is certified that error appears in the above-identified patent and that said Letters Patent are hereby corrected as shown below:

Column 3, line 25, "tranparent" should read -- transparent --.

Column 5, line 52, "averae" should read -- average --.

Column 7, line 53, "4.45$C_6$" should read -- 4.45 grams $C_6$ --.

Signed and Sealed this

Nineteenth Day of April 1977

[SEAL]

Attest:

RUTH C. MASON
*Attesting Officer*

C. MARSHALL DANN
*Commissioner of Patents and Trademarks*